(12) United States Patent
Choudhury

(10) Patent No.: US 12,070,408 B2
(45) Date of Patent: Aug. 27, 2024

(54) POSITIONING ATTACHMENT FOR A PATIENT

(71) Applicant: Concepto LLC, Cincinnati, OH (US)

(72) Inventor: Sambhu N. Choudhury, Cincinnati, OH (US)

(73) Assignee: Concepto LLC, Cincinnati, OH (US)

(*) Notice: Subject to any disclaimer, the term of this patent is extended or adjusted under 35 U.S.C. 154(b) by 456 days.

(21) Appl. No.: 17/165,265

(22) Filed: Feb. 2, 2021

(65) Prior Publication Data

US 2021/0154040 A1 May 27, 2021
US 2023/0201022 A9 Jun. 29, 2023

Related U.S. Application Data

(63) Continuation of application No. 15/866,661, filed on Jan. 10, 2018, now abandoned, and a continuation-in-part of application No. 15/369,511, filed on Dec. 5, 2016, now abandoned.

(60) Provisional application No. 62/263,448, filed on Dec. 4, 2015.

(51) Int. Cl.
| | |
|---|---|
| *A61F 5/37* | (2006.01) |
| *A61F 9/04* | (2006.01) |
| *A61F 13/02* | (2024.01) |
| *A61G 13/02* | (2006.01) |
| *A61G 13/12* | (2006.01) |

(52) U.S. Cl.
CPC .............. *A61F 5/37* (2013.01); *A61F 5/3761* (2013.01); *A61F 9/04* (2013.01); *A61F 13/02* (2013.01); *A61G 13/121* (2013.01); *A61G 13/1235* (2013.01); *A61G 13/02* (2013.01); *A61G 13/1205* (2013.01)

(58) Field of Classification Search
CPC .. A61F 5/00; A61F 5/37; A61F 5/3707; A61F 5/3715; A61F 5/3723; A61F 5/373; A61F 5/3738; A61F 5/3761; A61F 5/3769; A61F 5/3792; A61F 13/0203; A61B 46/00; A61B 46/20; A61B 46/40; A61B 2046/201
USPC ......................................................... 128/858
See application file for complete search history.

(56) References Cited

U.S. PATENT DOCUMENTS

| | | | |
|---|---|---|---|
| 6,572,541 B1* | 6/2003 | Petersvik | A61B 17/0293 |
| | | | 600/233 |
| 2008/0039760 A1* | 2/2008 | Lesko | A61F 13/0203 |
| | | | 602/42 |
| 2013/0133668 A1* | 5/2013 | Fisher | A61F 5/03 |
| | | | 128/845 |

* cited by examiner

*Primary Examiner* — Ophelia A Hawthorne
*Assistant Examiner* — Gina McCarthy
(74) *Attorney, Agent, or Firm* — Jenei LLC

(57) ABSTRACT

A method includes positioning a patient on a surgical support structure having a fixture. The method includes attaching, to a portion of a body of the patient, a first adhesive layer on a widened pad end of a surgical restraint device. The method includes extending an elongate strap member of the surgical restraint device in a direction in which the portion of the body of the patient is to be moved relative to a remaining portion of the body using tension in the elongate strap member. The method includes attaching an attachment end of the elongate strap member to the fixture of the surgical patient support structure to maintain the moved portion of the body in tension, exposing a surgical site on the body.

6 Claims, 9 Drawing Sheets

POSITIONING ATTACHMENT FOR A PATIENT

RELATED APPLICATIONS

This application is a continuation of U.S. patent application Ser. No. 15/866,661 entitled "POSITIONING ATTACHMENT FOR A PATIENT" filed 10-Jan.-2018, which in turn is a continuation-in-part of U.S. patent application Ser. No. 15/369,511 entitled "POSITIONING ATTACHMENT FOR A PATIENT" filed 5-Dec.-2016, which in turn claims the benefit of U.S. Provisional Application Ser. No. 62/263,448, entitled "POSITIONING ATTACHMENT FOR A PATIENT" and filed Dec. 4, 2015. The entire disclosures of which are hereby incorporated by reference for all purposes.

BACKGROUND OF THE INVENTION

1. Field of the Invention

The field of art disclosed herein generally pertains to a method of using patient surgical restraining devices, and more particularly to immobilizing portions of a patient's body to a surgical support surface during surgery.

2. Description of the Related Art

Often a patient who is placed onto an operating table is positioned in a predetermined way on the table to allow for surgical intervention. This position must be maintained during the surgery with very little motion to the body parts.

Patient position restraining systems are of multiple varieties. Some are silicone based pads that allow for a body part to have limited specific point of pressure to avoid decubitus. Some are foam based to allow a similar alteration of pressure on a body part to prevent compression and ulceration or damage to the skin in long or even short procedures.

Retaining straps may be used along the patient's body to secure the patient to the underlying table. Often the patient is moved aggressively or the table may be tilted. In these situations, there is a need to protect the body with straps so that the patient does not literally fall from the operating table. Although there are soft and malleable cushion straps that can be used, often high tension materials are used so that firm pressure can be applied to a sometimes massive torso to allow for firm fixation. In this situation if there is any change in body position, the pads or foams that are positioned under the straps may become dislodged and friction skin damage may occur.

In any situation where there is patient motion during the case, the initial positions of the arms, legs, bony prominences may change and thus potentially altering the ability to protect the body part with non-sticky foam cushions. Even in the cases of the vacuum positioning system which custom forms to the body or body part, alterations can occur with resultant changes in the pressure that the body parts experience.

In situations in which a body part such as the arm has to be pulled to one side of the body, foam straps are applied with underlying cords of non-woven or cloth attachments straps. These have a significant ability to strangulate the body part during a procedure regardless of the foam used. This is often worse in a morbidly obese individual with a more difficult limb to control. In a debilitated or older individual with poor skin, even minor abrasions can result in full skin sloughs.

In the morbidly obese individual, multiple skin flaps are the rule rather than the exception. The skin must be pulled to one side to allow for the surgery to take place without contamination and with maximum visibility. Conventionally, this situation is dealt with by tape that is attached to the patient skin to allow for an attachment to the pannus. The other side of the tape may be then attached with tension to the side of the bed. Similar skin tension is necessary when dealing with surgeries below the breast or around the neck or lower face.

In situations in which there is traction applied to an extremity through a traction device, such as during wrist, shoulder or ankle arthroscopy, the attachment points are again related to straps and a mobile silicone or foam based attachment.

Prior inventors have addressed the above problems. Representative prior U.S. patents are listed below.

In U.S. Pat. No. 3,845,757, a pre-gelled intensive care electrode is formed from two layers of soft, conformable foam material having a rigid plastic supporting layer between the foam layers. A conductive connector is in contact with an open-celled spongy material filled with an electrolyte which provides means for connecting the electrode to monitoring devices and measuring the electrical impulses from a patient's skin. The biomedical monitoring electrode is held in place on the patient's skin by means of a hypo-allergenic pressure sensitive adhesive.

U.S. Pat. No. 4,016,869 discloses a signal collector system, in particular for electrical body signals, consisting of at least one electrode and a contact paste which is to be introduced, at the applicating location, intermediate the body and the electrode. The electrode provides for the extensive avoidance of the effect of the forces and twisting moments which attack it in its applied condition by forming on the body a homogeneous contact paste and adhesive with a conductive substance having a salve or syrup like consistency for the electrode.

In U.S. Pat. No. 4,008,721, a tape form electrode is provided which is usable for transmission of electrical signals into the human body through the skin. The electrode is of a construction so that it can be applied to the skin to secure good electrical contact therewith and remain in place for many days despite normal movement and the normal activities of the subject such as perspiring, and washing. The construction utilizes a porous backing material which has an adhesive layer on one side thereof and over the adhesive layer a second layer which has incorporate therein a quantity of finely divided silver metal. The composition construction is of a thickness and selection of materials such that it readily "breaths" thereby permitting escape of normal amounts of perspiration from the skin of the subject. The adhesive is normally "dry" and is activated at the time of application by a suitable solvent.

U.S. Pat. No. 3,911,906 discloses an electrode device for establishing an electrical connection between electromedical apparatus and the skin of the human anatomy comprising a composite electrode body for self-adhering engagement with a substantial surface area of the skin to establish the electrical connection throughout substantially the entire engaged area of the skin without the use of conductive pastes, gels or other liquids, such as solvents or the like, the composite electrode body being porous and hypoallergenic and including a carrier layer and a thin flexible layer of pressure sensitive adhesive material having fine electrically conductive particles dispersed throughout providing a tacky skin-engaging surface the particles being provided in an amount sufficient to effect the electrical connection with the engaged area of the skin through the layer by particle to particle contact while permitting the skin-engaging surface of the layer to remain tacky prior to skin engagement. A removable sheet having a release surface engaging the tacky skin-engaging surface of the layer is operable to be separated therefrom prior to application without substantially reducing the tackiness thereof.

In U.S. Pat. No. 4,066,078, an improved combination electrode for use in medical applications requiring monitoring and stimulation is provided preferably having an electrical current conductor including a connector in addition to a skin-interfacing film wherein this film may have adhesive, plastic and hydrophilic properties such as may reside in an electrically conductive, polymeric composition.

SUMMARY OF THE INVENTION

In another aspect, the present disclosure provides a device for immobilizing a portion of a patient. The device includes a patch having an adhesive gel surface suitable for adhering to the skin of the patient.

In one aspect of the present innovation, a surgical restraint device includes an elongate strap member having a widened pad end and an attachment end. An adhesive layer is affixed to one side of the widened pad end that is formed of a hypoallergenic material for selective engagement to skin of a patient. A peel-off layer releasably covers the adhesive layer. At least one aperture formed in the attachment end to accept engagement to a hooking member presented on a surgical patient support structure.

In another aspect of the present innovation, an adhesive eye patch includes an inner covering shaped to encircle an orbit of a patient's eye and comprising an extending tab for manually grasping and peeling the inner covering away from a patient's face and comprising an aperture sized to encompass a patient's eye. An intermediate eye protective layer is attached to an outer side of the inner covering to cover the aperture and formed of a material that is protective or noninteractive with the patient's eye. An over covering is peripherally attached to the outer side of the inner covering around and overtop of the intermediate eye protective layer. An adhesive layer is at least intermittently adhered around an inner periphery of an inner side of inner covering to adhere to skin around a patient's eye. A peel-off layer is releasably covering the adhesive layer before adhering to the face of the patient.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE FIGURES

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

In one aspect, the present disclosure provides a silicone type of protectant with an adhesive pad that can attach to a body part in the operating room. This can allow for control of the body and manipulation of the body part without skin damage from straps or tape.

In another aspect, the straps may be attached to the gel pad so that the body part may be manipulated into a better position while allowing the silicone to protect the skin area in question by acting as another layer of protective medium.

In another aspect, the straps may be attached to the bed with an adjustable hook and loop assembly method or some other potential securing method including iterating using glue, buttons, belt buckle like attachments.

In another aspect, the straps may be adjusted during the case but are not sterile at the attachment points to the bed.

Another iteration may include a suitable sterile gel matrix that allows for use in the operating field.

In an exemplary embodiment, one surface of the pad has an adhesive gel applied thereto. The gel is designed to adhere to the skin, and is preferably initially covered with a tear-away covering. Suitable adhesive gels are well known. The adhesion strength can be altered by suitable choice of materials, according to the intended application. The strap end of the device is provided with fasteners such as soft loops/stiff hooks, adhesive material knots, eyelets, etc., so that it can be wrapped around a fixture and secured in place. The pad is preferably divided into parallel sections which can be splayed when desired to distribute the adhesive traction over a larger area of the patient.

Similarly, an eye patch embodies the principles of the aspects of the present innovation can be used to immobilize the eyelid. The eye patch comprises an outer layer, a protective material, and an inner layer provided with a pull tab. Adhesive dots and an adhesive line are applied to the reverse of the inner layer. A release material might initially cover the adhesive.

Turning now to the Drawings, the detailed description set forth below in connection with the appended drawings is intended as a description of various configurations and is not intended to represent the only configurations in which the concepts described herein may be practiced. The detailed description includes specific details for the purpose of providing a thorough understanding of various concepts with like numerals denote like components throughout the several views. However, it will be apparent to those skilled in the art that these concepts may be practiced without these specific details. In some instances, well known structures and components are shown in block diagram form in order to avoid obscuring such concepts.

Figure 1:
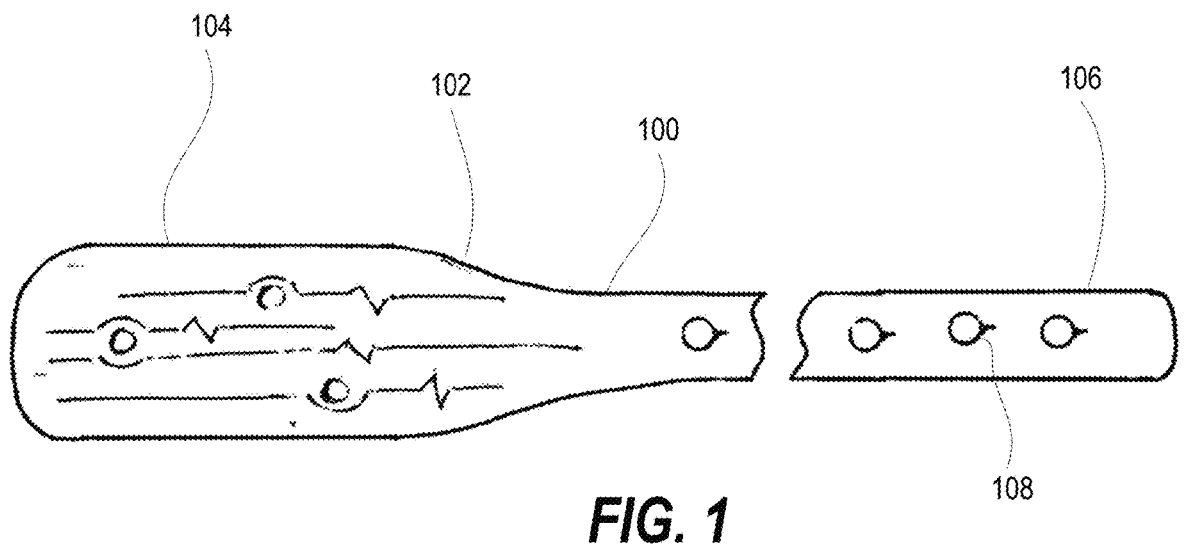
FIG. 1 illustrates a front view of an example patient positioning device including an adhesive pad attached to strap for attachment to a surgical platform for fixation, according to one or more embodiments.

Referring to the FIG. 1, in an exemplary embodiment of a patient positioning device 100 that includes a strap 102 having a widened pad end 104 at one end and an elongate attachment end 106. Apertures 108 formed along the length of the attachment end 106 provide an opening for hooking to a fixed structure, such as to a surgical support structure.

Figure 2:
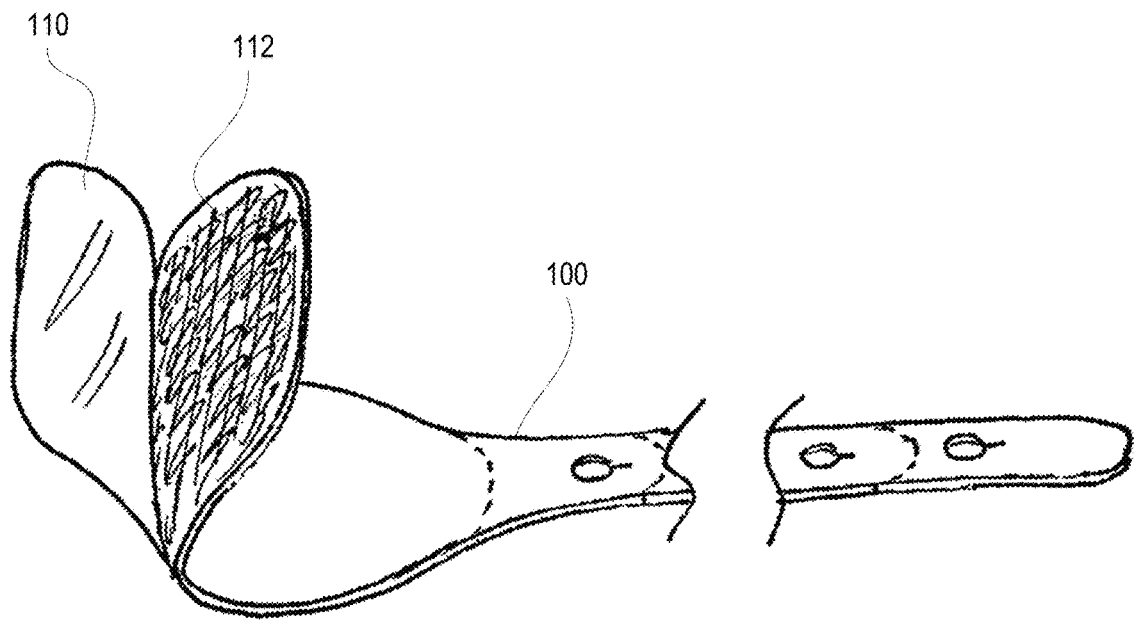
FIG. 2 illustrates an isometric detail view of the example patient positioning device of FIG. 1 having a pull-off protective cover being removed from a pad end, according to one or more embodiments.
Figure 3:
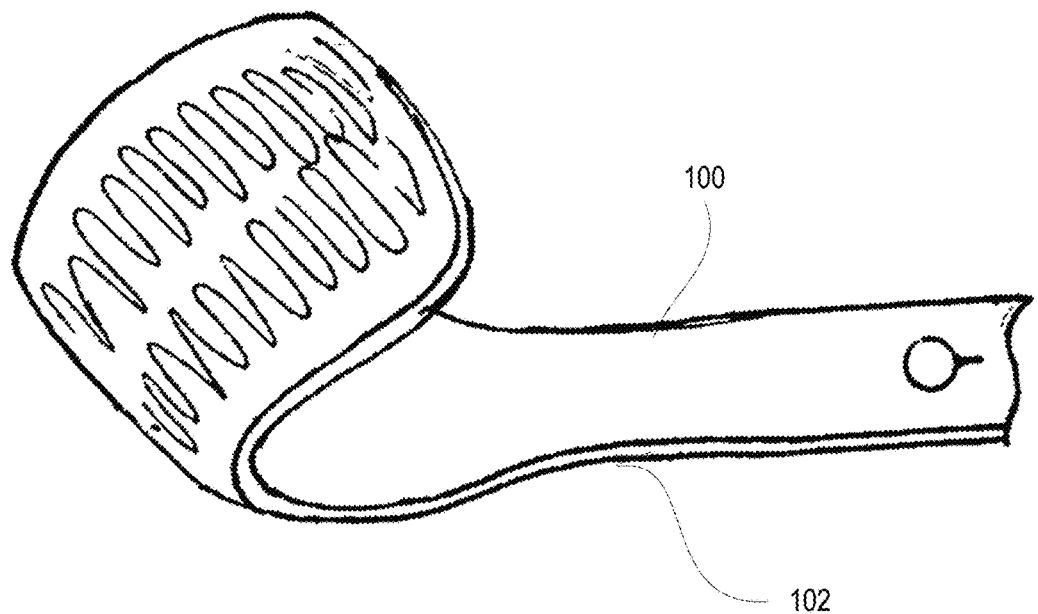
FIG. 3 is an isometric detail view of a portion of the patient positioning device of FIG. 1, with an end turned up to reveal a gel sticky surface of the pad end, according to one or more embodiments.

FIG. 2 illustrates a peel-off protective covering layer 110 being removed from one side of the widened pad end 104 of the patient positioning device 100 to expose a hypoallergenic adhesive layer 112 which comprises a gel sticky surface providing sufficient adherence in sheer to be secured to the skin. The gel sticky surface readily allows removal from the skin when pulled away from the skin. FIG. 3 illustrates that the strap 102 is formed of a flexible material to conform to the shape of the patient. In one or more embodiments the strap 102 is formed from a resilient material. In one or more embodiments the strap 102 is formed of an inelastic material.

Figure 4:
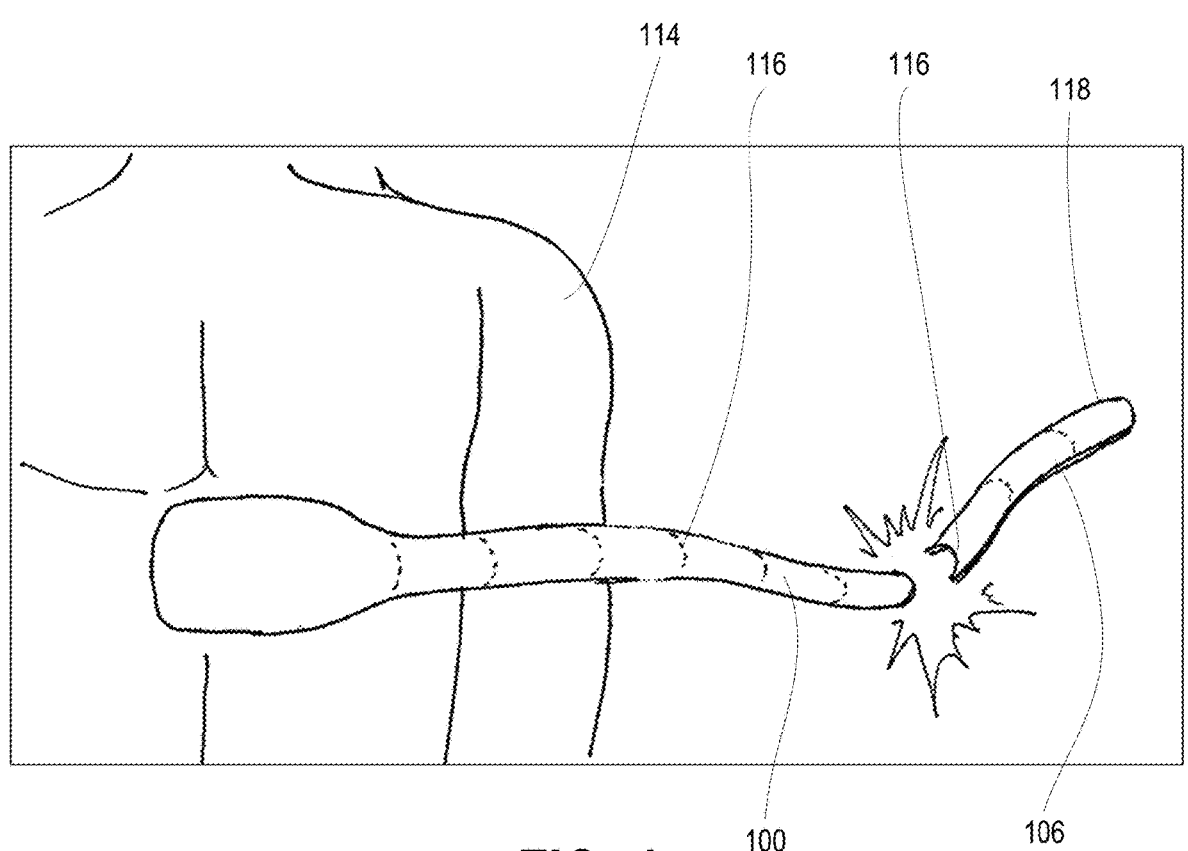
FIG. 4 illustrates a front side view of the example patient positioning device of FIG. 1 having the gel stick surface of the pad end adhered to a chest of a patient and with an excess segmented portion strap selectively detached, according to one or more embodiments.

FIG. 4 illustrates that the example patient positioning device 100 having the pad end 104 adhered to a chest portion of a patient 114. The attachment end 106 includes transverse grooves 116 that facilitate manual separation of an excess distal length 118 of the attachment end 106 that is not needed.

Figure 5:
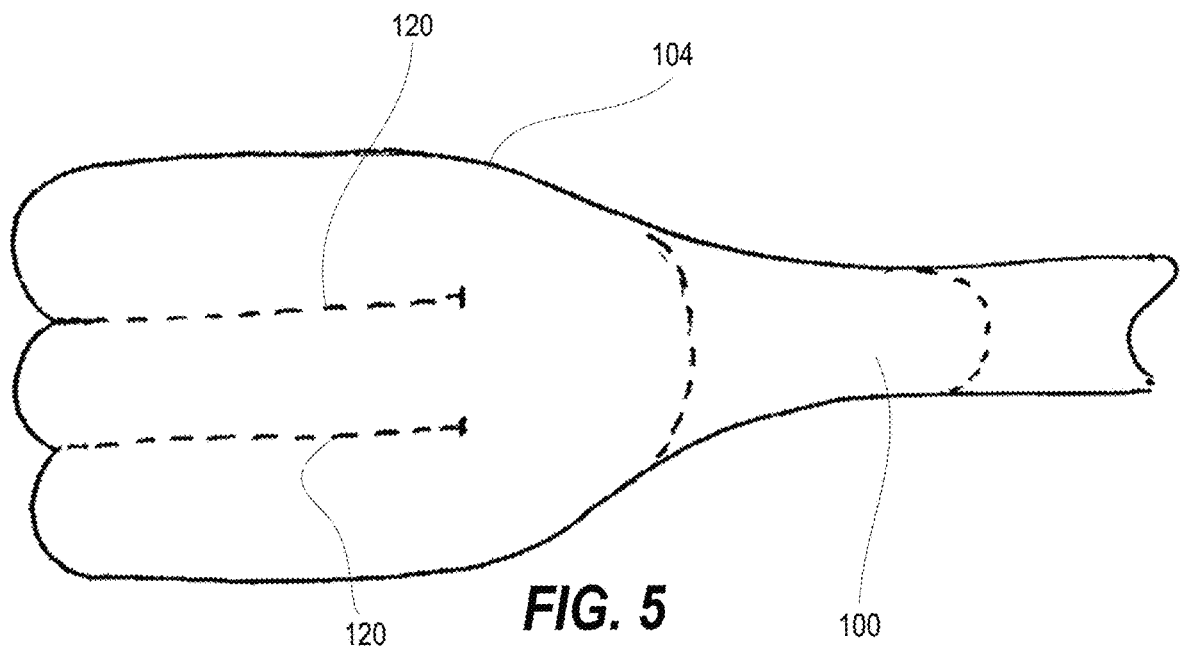
FIG. 5 illustrates a front view of an example patient positioning device including frangible, tracks formed in a pad end, according to one or more embodiments.
Figure 6:
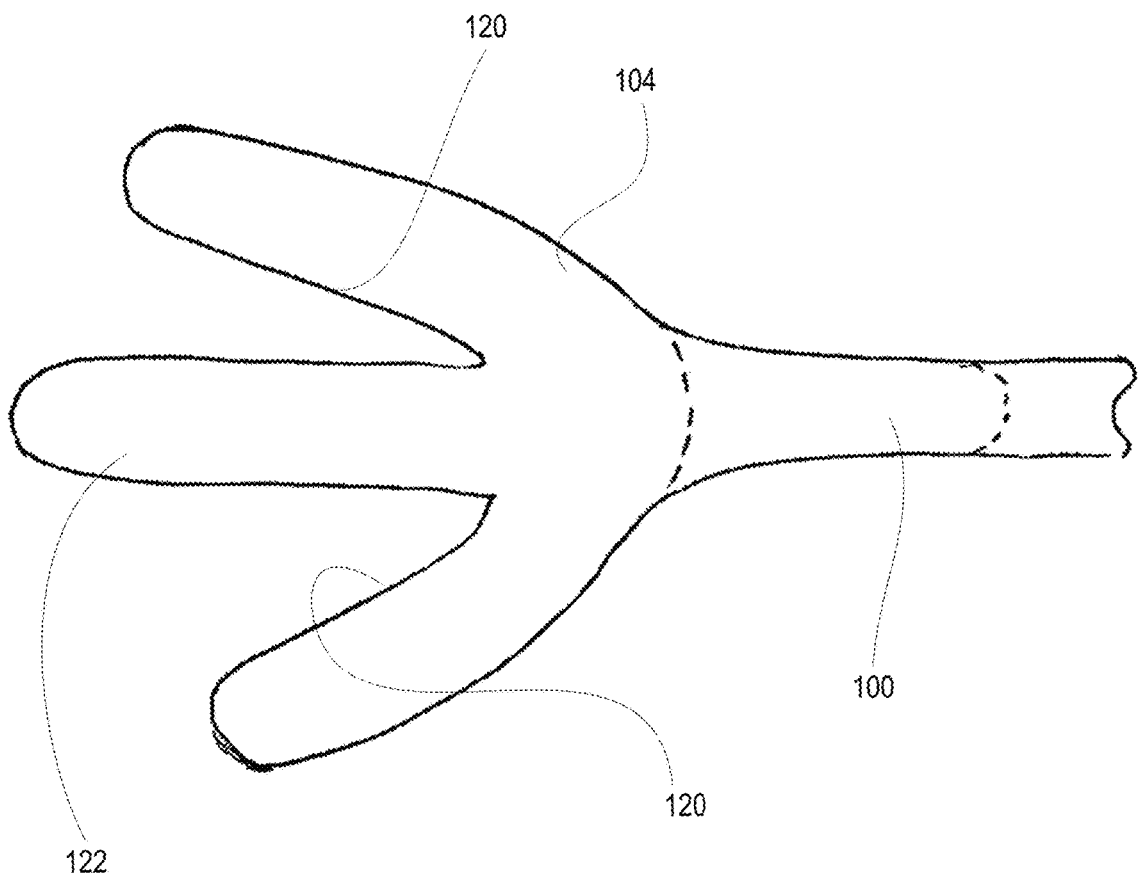
FIG. 6 illustrates a front view of the example patient positioning device of FIG. 5 with the frangible tracks opened to expandingly separate fingers of the pad end, according to one or more embodiments.

FIG. 5 illustrates that the example patient positioning device 100 can include frangible, tracks 120 formed in a pad end 104 that are initially unbroken to provide a unitary pad end 104. FIG. 6 illustrates the example patient positioning device 100 with the frangible tracks 120 opened to expandingly separate fingers 122 of the pad end 104.

Figure 7:
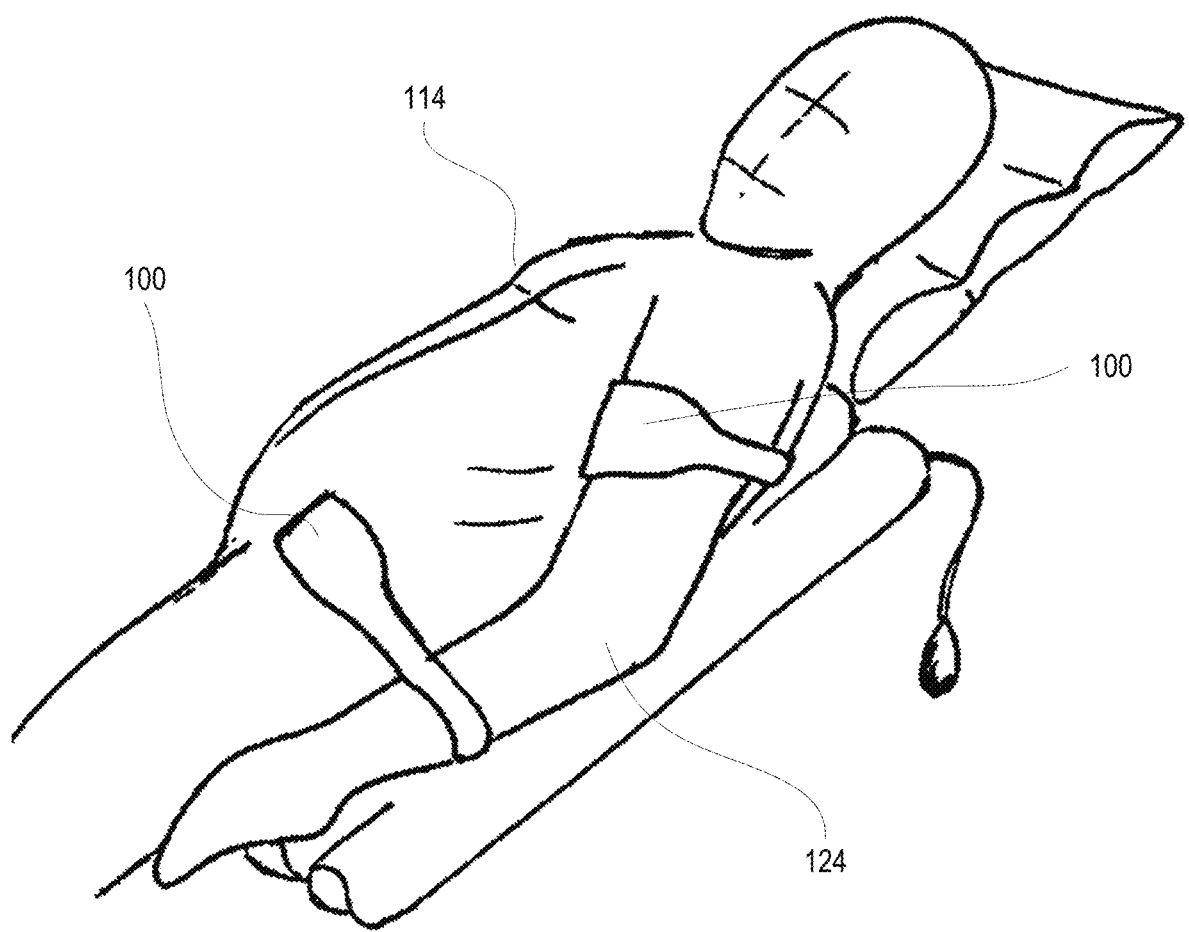
FIG. 7 illustrates a side view of two example patient positioning devices of FIG. 1 positioning an arm of a patient to other parts of the patient, according to one or more embodiments.
Figure 8:
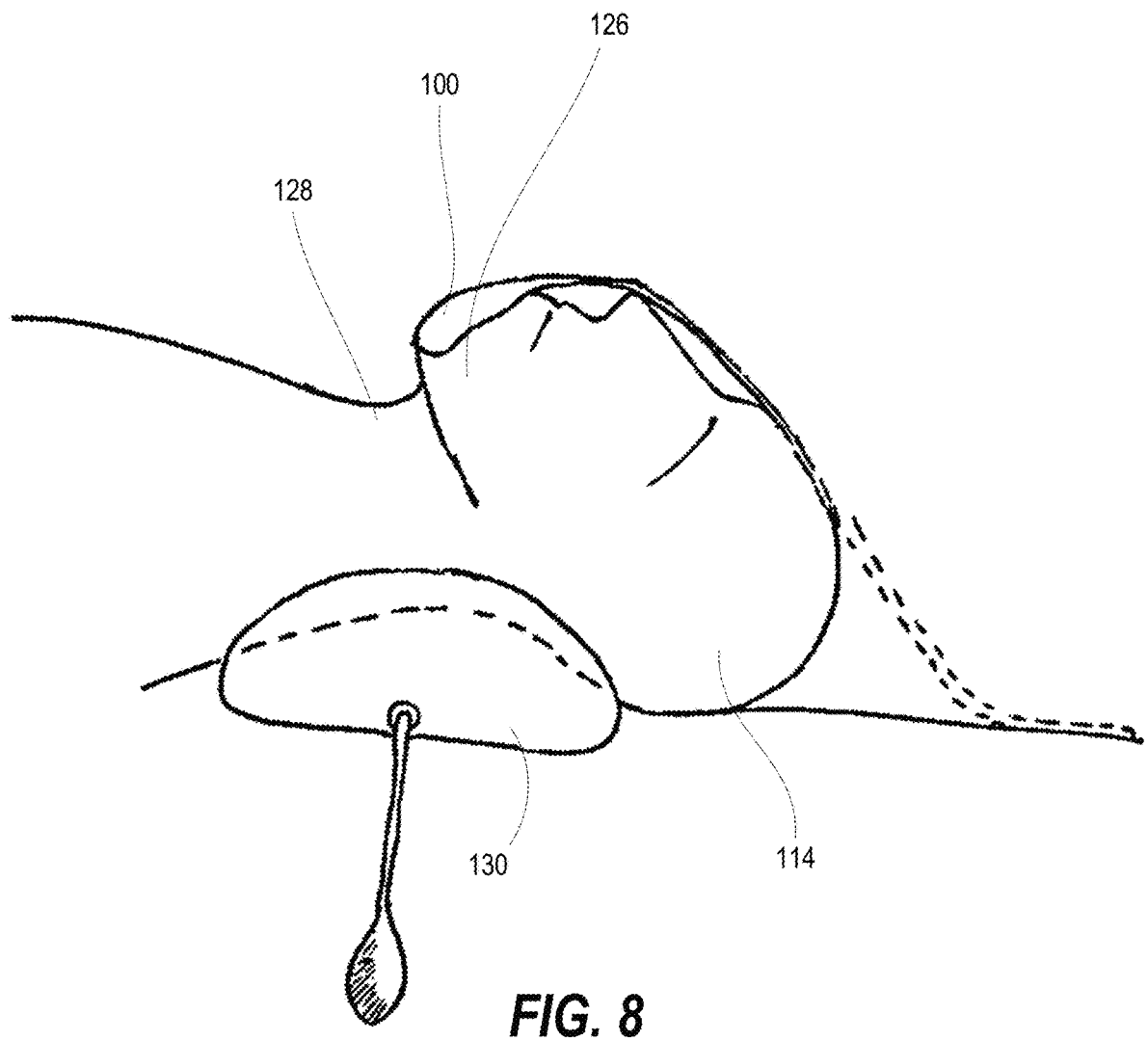
FIG. 8 illustrates a side view of the example patient positioning devices of FIG. 1 adhered to a chin of a patient to expose a neck portion thereby allowing an unimpeded view of an intended surgical site, according to one or more embodiments.
Figure 9:
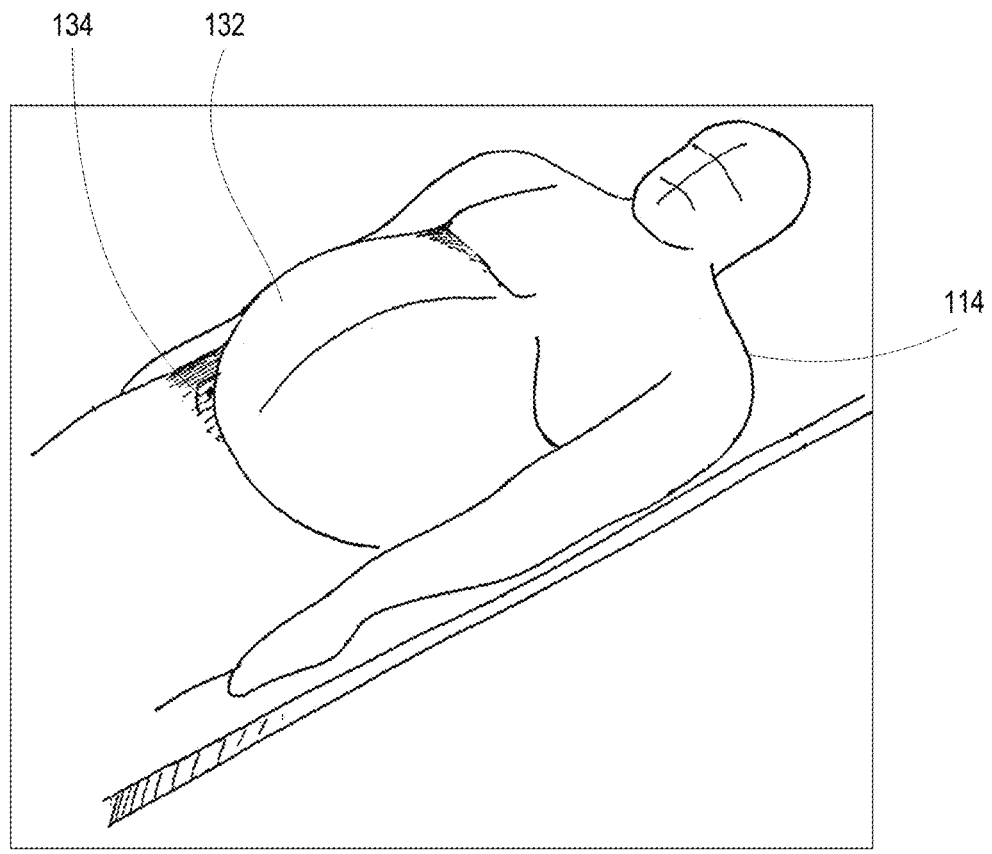
FIG. 9 illustrates a top isometric view of a patient having a large abdomen, obscuring a surgical site at waist level.
Figure 10:
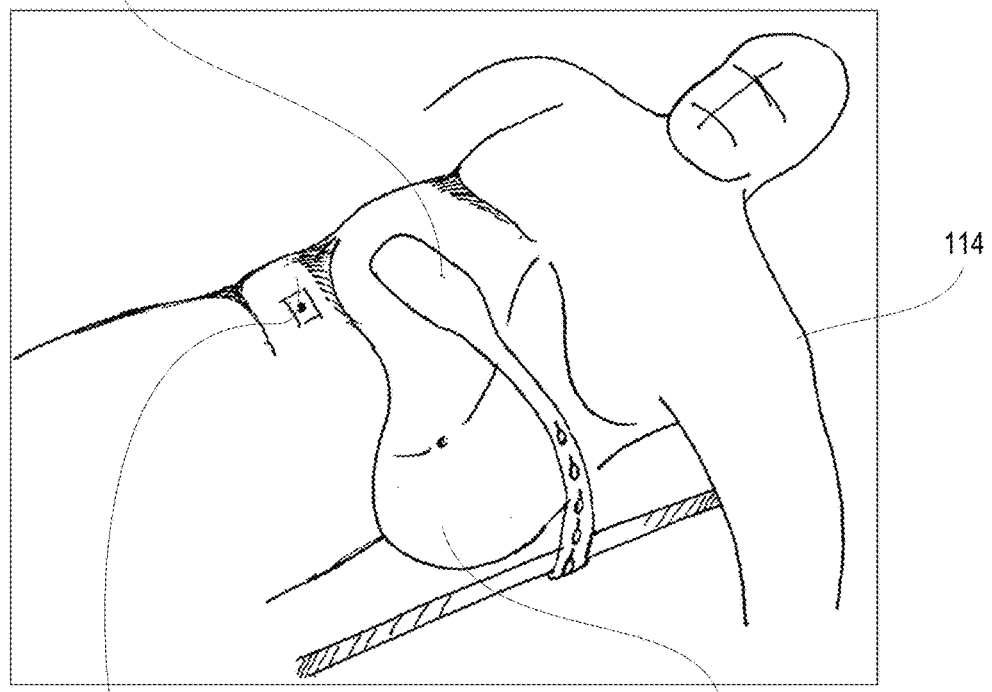
FIG. 10 illustrates a top isometric view of the patient of FIG. 9 having the example patient positioning devices of FIG. 1 retracting the abdomen away from the operative site, according to one or more embodiments.

FIG. 7 illustrates two example patient positioning devices 100 positioning an arm 124 of a patient 114 to other parts of the patient 114. FIG. 8 illustrates the example patient positioning device 100 adhered to a chin 126 of a patient 116 to expose a neck portion 128 thereby allowing an unimpeded view of an intended surgical site. The patient 114 is also supported by an inflatable pillow 130 under the neck. FIG. 9 illustrates a patient 114 having a large abdomen 132, obscuring a surgical site 134 at waist level. FIG. 10 illustrates the example patient positioning device 100 retracting the abdomen 132 away from the operative site 134.

Figure 11:
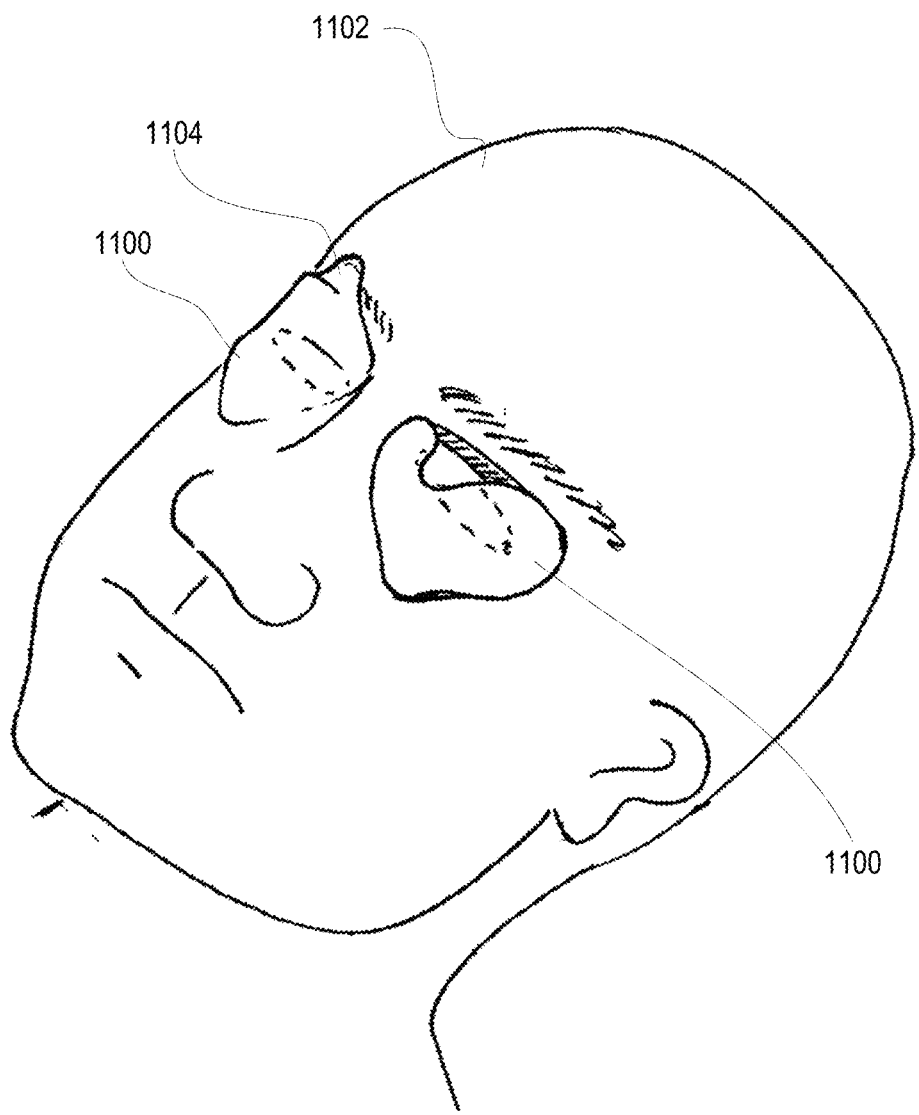
FIG. 11 illustrates a top side view of an example pair of adhesive eye patches applied to a patient, according to one or more embodiments.
Figure 12:
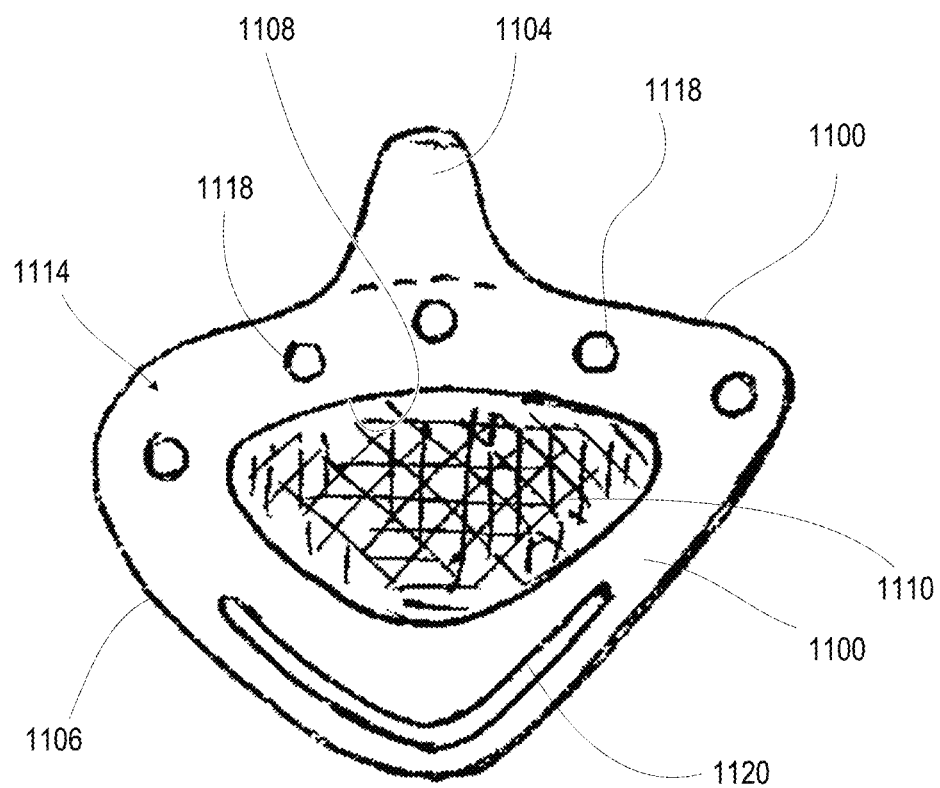
FIG. 12 is a rear view the example adhesive eye patch, according to one or more embodiments.
Figure 13:
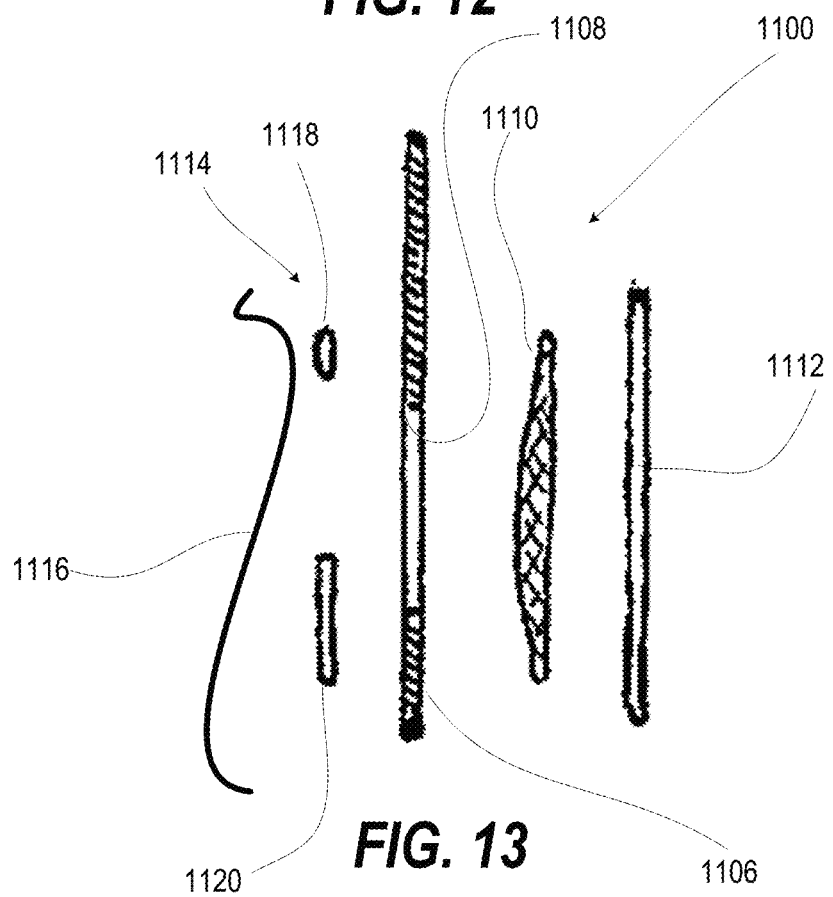
FIG. 13 is an side exploded side view of the example adhesive eye patch of FIG. 10, according to one or more embodiments.
Figure 14:
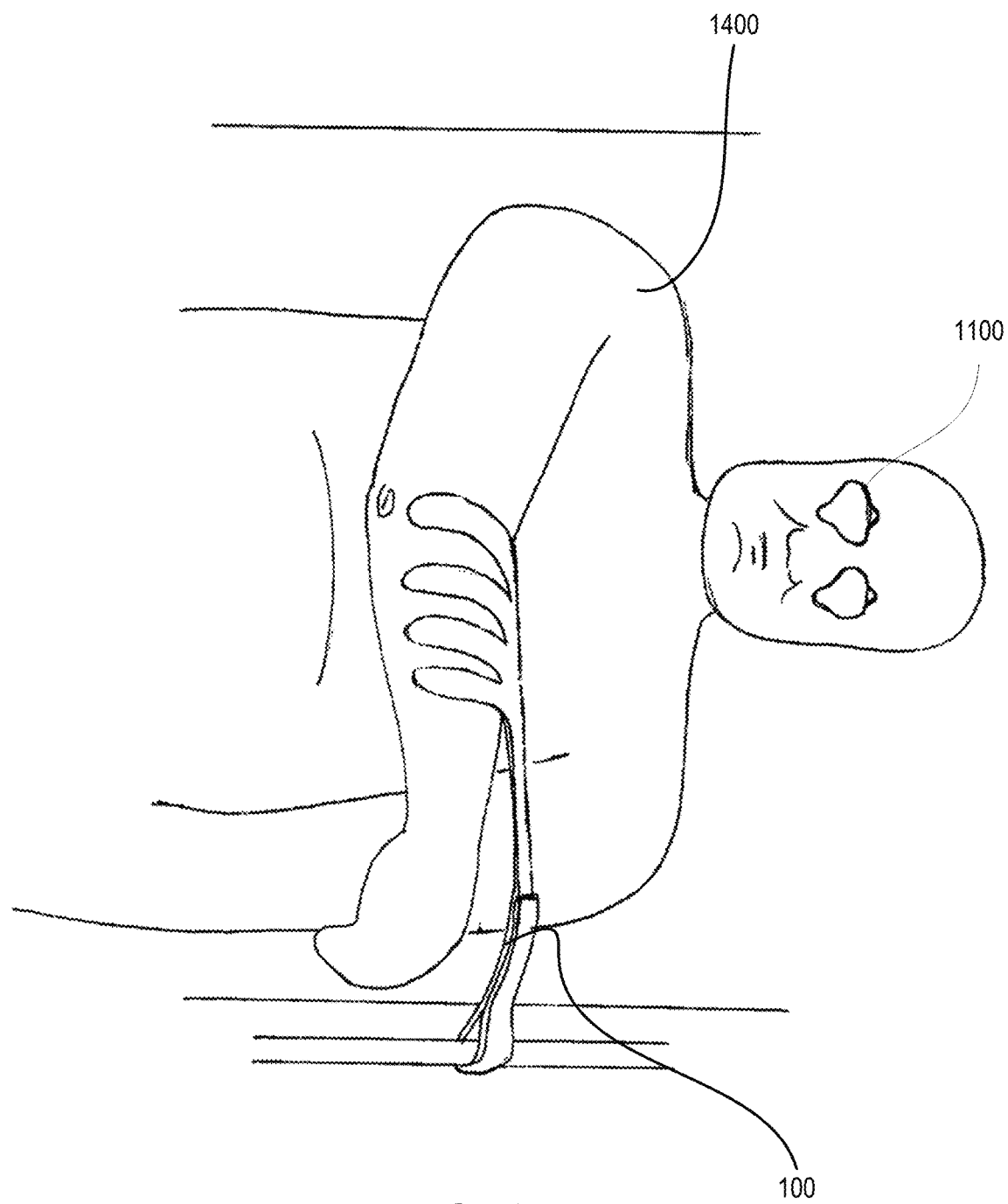
FIG. 14 illustrates a side view of a patient secured with the example patient positioning devices of FIG. 1 and the example adhesive eye patch of FIG. 10, according to one or more embodiments.

FIG. 11 illustrates an example pair of adhesive eye patches 1100 applied to each eye of a patient 1102, removable by pulling on a tab 1104 extending from one edge. FIGS. 12-13 illustrate that the adhesive eye patch 1100 includes an inner covering 1106 shaped to encircle an orbit of a patient's eye and comprising the extending tab 1104 for manually grasping and peeling the inner covering away from a patient's face and having an aperture 1108 sized to encompass a patient's eye. An intermediate eye protective layer 1110 is attached to an outer side of the inner covering 1106 to cover the aperture 1108 and is formed of a material that is protective or noninteractive with the patient's eye. An over covering 1112 (FIG. 12) is peripherally attached to the outer side of the inner covering 1106 around and overtop of the intermediate eye protective layer 1110. An adhesive layer 1114 is at least intermittently adhered around an inner periphery of an inner side of inner covering 1106 to adhere to skin around a patient's eye. A peel-off layer 1116 releasably covers the adhesive layer 1114 before adhering to the face of the patient. In an exemplary embodiment, the adhesive layer 1114 comprises a series of space apart adhesive dots 1118 positioned for adhering above the patient's eye and an arcing line 1120 of adhesive positioned for adhering below a patient's eye. FIG. 14 illustrates a patient 1400 secured with the example patient positioning device 100 and the example adhesive eye patch 1100.

All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that terms is utilized.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A method comprising: positioning a patient on a surgical support structure having a fixture; attaching, to a portion of a body of the patient, a first adhesive layer on a widened pad end of a surgical restraint device; extending an elongate strap member of the surgical restraint device in a direction in which the portion of the body of the patient is to be moved relative to a remaining portion of the body using tension in the elongate strap member; attaching an attachment end of the elongate strap member to the fixture of the surgical patient support structure to maintain the moved portion of the body in tension, exposing a surgical site on the body, wherein the surgical restraint device includes at least three parallel sections with frangible tracks in the widened pad end that are initially unbroken to provide a unitary pad end, and wherein prior to the step of: attaching, to a portion of a body of the patient, a first adhesive layer on a widened pad end of a surgical restraint device, separating and splaying out the widened pad end using the at least three parallel sections with the frangible tracks opened and expanded as at least three separate fingers of the widened pad to distribute traction over a large area of the patient, wherein the widened pad is separated into fingers configured to expand an area of skin adhered to the surgical restraint device.

2. The method of claim 1, wherein attaching the attachment end to the fixture comprises looping the attachment end around the fixture and adhering the attachment end to the elongate strap member.

3. The method of claim 1, further comprising removing a release layer that initially covers the adhesive layer on the widened pad end prior to attaching to the portion of the body of the patient.

4. The method of claim 1, wherein the elongate strap member comprises frangible grooves formed from an exterior edge toward the attachment end.

5. The method of claim 1, wherein positioning the patient on the surgical patient support structure comprises placing the patient on a selected one of: (i) a bed; and (ii) an operating table.

6. The method of claim 1, wherein attaching the attachment end of the elongate strap member comprises hooking the fixture through an aperture in the attachment end of the elongate strap member.

* * * * *